United States Patent
Stanish

(10) Patent No.: US 6,585,762 B1
(45) Date of Patent: Jul. 1, 2003

(54) ARTERIOVENOUS GRAFTS AND METHODS OF IMPLANTING THE SAME

(76) Inventor: Paul Stanish, 11356 Morton Ct., Crown Point, IN (US) 46307

( * ) Notice: Subject to any disclaimer, the term of this patent is extended or adjusted under 35 U.S.C. 154(b) by 96 days.

(21) Appl. No.: 09/704,083

(22) Filed: Nov. 1, 2000

Related U.S. Application Data

(60) Provisional application No. 60/224,392, filed on Aug. 10, 2000.

(51) Int. Cl.⁷ .................................................. A61F 2/06
(52) U.S. Cl. ........................ 623/1.3; 623/1.31; 606/108; 606/153
(58) Field of Search ........................... 623/13.11, 1.32, 623/1.31, 1.37, 1.35, 1.24, 1.15, 1.13, 1.2, 1.16, 1.3; 606/153, 191, 108; 128/898; 604/8, 175; 138/118; 264/138, 443

(56) References Cited

U.S. PATENT DOCUMENTS

| | | | |
|---|---|---|---|
| 2,127,903 A | * 8/1938 | Bowen ........................ 138/118 |
| 3,044,497 A | 7/1962 | Rebut |
| 3,683,926 A | 8/1972 | Suzuki |
| 3,818,511 A | 6/1974 | Goldberg et al. |
| 4,441,215 A | * 4/1984 | Kaster ........................ 623/1.37 |
| 4,503,568 A | * 3/1985 | Madras ........................ 623/1.3 |
| 4,512,761 A | 4/1985 | Raible |
| 4,728,328 A | * 3/1988 | Hughes et al. .............. 623/1.32 |
| 4,957,669 A | 9/1990 | Primm |
| 5,425,738 A | * 6/1995 | Gustafson et al. .......... 606/151 |
| 5,443,497 A | 8/1995 | Venbrux |
| 5,456,714 A | * 10/1995 | Owen ............................ 604/8 |
| 5,527,324 A | 6/1996 | Krantz et al. |
| 5,609,605 A | * 3/1997 | Marshall et al. ............. 606/191 |
| 5,653,743 A | * 8/1997 | Martin ........................ 606/153 |
| 5,683,449 A | * 11/1997 | Marcade ....................... 128/898 |
| 5,725,572 A | * 3/1998 | Lam et al. ....................... 600/3 |
| 5,755,778 A | 5/1998 | Kleshinski |
| 5,769,870 A | 6/1998 | Salahieh et al. |
| 5,800,520 A | 9/1998 | Fogarty et al. |
| 5,843,169 A | * 12/1998 | Taheri ........................... 606/108 |
| 5,849,036 A | * 12/1998 | Zarate ........................ 623/1.31 |
| 5,910,168 A | 6/1999 | Myers et al. |
| 5,944,730 A | * 8/1999 | Nobles et al. ............... 606/151 |
| 5,976,159 A | * 11/1999 | Bolduc et al. .............. 606/104 |
| 5,979,455 A | 11/1999 | Maginot |
| 6,016,810 A | 1/2000 | Ravenscroft |
| 6,019,788 A | 2/2000 | Butters et al. |
| 6,098,630 A | * 8/2000 | Papazoglou .............. 123/198 D |
| 6,261,255 B1 | 7/2001 | Mullis et al. |
| 6,338,724 B1 | 1/2002 | Dossa |
| 6,371,981 B1 | 4/2002 | Yang et al. |

OTHER PUBLICATIONS

Agarwal, Rajiv; Davis, Joyce L., Aug. 1999, Journal of Kidney Diseases, 34(2):212–217.*
Instructions for Use for Gore Tex® Vascular Grafts ( Jun. 1998) W.L. Gore & Associates, Inc., Flagstaff, Arizona.
Information for Use Venaflo™ ePTFE Vascular Gaft and Venaflo Graft with Carbon ( Feb. 1998) by IMPRA, Inc., Tempe, Arizona, EEA Authorized Representative C.R. Bard Ireland Ltd., Parkmore Industrial Estate, Galway, Ireland.
Information for Use of Carbaflo® Grafts and ePTFE Vascular Grafts (6/99) IMPRA, Inc., a Subsidiary of C.R. Bard, Inc., Tempe, Arizona.

(List continued on next page.)

Primary Examiner—Paul B. Prebilic
Assistant Examiner—Crystal Gilpin
(74) Attorney, Agent, or Firm—Woodard, Emhardt, Moriarty, McNett & Henry LLP

(57) ABSTRACT

The invention provides arteriovenous grafts and methods for implanting the same. In one aspect of the invention, there are provided arteriovenous grafts that have a stepped down venous end. In another aspect, the invention provides arteriovenous grafts having cuffs for attachment to a target vein. The invention also provides methods for implanting arteriovenous grafts that include inserting the venous end of a graft into the target vein for positioning downstream of the venotomy site.

50 Claims, 3 Drawing Sheets

OTHER PUBLICATIONS

Back, Martin R.; White, Rodney A., *The Biologic Response of Prosthetic Dialysis Grafts*, Vascular Access (1997) pp. 137–148.

Cinat, Marianne E.; Hopkins, Judith and Wilson, Samuel E., *A Prospective Evaluation of PTFE Graft Potency and Surveillance Techniques in Hemodialysis Access*, Annals of Vascular Surgery (1999) 13(2):191–198.

Coulson, Alan S.; Singh, Jagjit; Moya, Joseph C., *Modification of Venous End of Dialysis Grafts: An Attempt to Reduce Neointimal Hyperplasia*, Dialysis and Transplantation (Jan. 2000) 29(1):10–18.

Coulson, Alan S., *Combination of Elephant Truck Anastomosis Technique and Vascular Clips for Dialysis Grafts*, The Seventh Biannual Symposium on Dialysis Access Vascular Access for Hemodialysis VII, pp. 19–26, May 4–5, 2000, San Antonio, Texas.

Deierhoi, Mark H., *Preliminary Results of an Aggressive Approach to Arteria Fistula Construction for Hemodialysis*, The Seventh Biannual Symposium on Dialysis Access, Vascular Access for Hemodialysis VII, May 4–5, 2000, San Antonio, Texas.

Eggers, Paul W., *Medicare Expenditures for Fistula, Graft, and Catheter–Access Procedures*, The Seventh Biannual Symposium on Dialysis Access, Vascular Access for Hemodialysis VII, May 4–5, 2000, San Antonio, Texas.

Hakim, Raymond and Himmelfarb, Jonathan, *Hemodialysis access failure: A call to action*, Kidney International, (1998) 54:1029–1040.

Halpin, Dermot P.; Stack, Michael M.; Knoll, Kraig and Gaskin, Thomas A., *Arteriovenous Graft Salvage in Hemodialysis Patients*, Ch. 17, pp. 153–157 (date unknown).

Kalman, Peter G.; Pope, Mark; Bhola, Cyndi; Richardson, Robert and Sniderman, Kenneth W., *A practical approach to vascular access for hemodialysis and predictors of success*, Journal of Vascular Surgery ( Oct. 1999) 30(4):727–733.

Kohler, Ted R.; Kirkman, Thomas R.; Kraiss, Larry W.; Zierler, Brenda K. and Clowes, Alexander W., *Increased Blood Flow Inhibits Neointimal Hyperplasia in Endothelialized Vascular Grafts*, Circulation Research, (Dec. 1991) 69(6):1557–1565.

Lumsden, Alan B., *Prospective, Randomized Multicenter Trial of Stepped Venaflo e–Polytetrafluoroethylene Grafts Compared with IMPRA Stepped e–Polytetrafluoroethylene Grafts in Hemodialysis*, The Seventh Annual Symposium on Dialysis Access, Vascular Access for Hemodialysis VII, May 4–5, 2000, San Antonio, Texas.

Lumsden, Alan B. and Chen, Changyi, *Accelerated Neointimal Hyperplasia in Hemodialysis Access Grafts*, (1997) Chapter 4, pp. 43–50.

Lumsden, Alan B., Macdonald, M. Julia; Kikeri, Deepak; Cotsonis, George; Harker, Laurence A. and Martin, Louis G., *Cost Efficacy of Duplex Surveillance and Prophylactic Angioplasty of Arteriovenous ePTFE Grafts*, Annals of Vascular Surgery, (1998) pp. 138–142.

Sands, J. and Miranda, C.L., *Increasing numbers of AV fistulas for hemodialysis access*, Clinical Nephrology (1997) 48(2):114–117.

Tordoir, Jan H.M.; Hofstra, Leo; Lemsen, Susan; Leunissen, Karel M.L.; Kitslaar, Peter J.E.H.M. and Daemen, Mar J.A.P., *Pathophysiology of Neointimal Hyperplasia: The Correlation Between Blood–Flow Parameters and Cellualar Proliferation in Stenotic Lesions Derived from Arteriovenous Fistulas*, Chapter 29, pp. 268–277 (date unknown).

Turitto, Vincent T. and Goldsmith, Harry L., *Rheology, Transport, and Thrombosis in the Circulation*, Vascular Medicine, a Textbook of Vascular Biology and Diseases, $2^{nd}$ Ed., Little Brown and Company, Boston, New York, Toronto and London, Chapter I, pp. 141–180 (1996).

Veldenz, Henry C.; Lenz, Barbara J.; Dennis, James W.; Khansarinia, Saeid and Atteberry, Linda R., *Superiority of Standard–Thickness PTFE Grafts in Hemodialysis Access*, (1997) Chapter 34, pp. 316–322.

Greisler, H., *Vascular Graft Healing—Interfacial Phenomena*, New Biologic and Synthetic Vascular Prosthesis, (1991) Chapter 1, pp. 1–19.

\* cited by examiner

ARTERIOVENOUS GRAFTS AND METHODS OF IMPLANTING THE SAME

REFERENCE TO RELATED APPLICATIONS

This application claims the benefit of U.S. Provisional Application No. 60/224,392, filed Aug. 10, 2000 and entitled ARTERIOVENOUS GRAFTS AND METHODS OF IMPLANTING THE SAME, which is hereby incorporated by reference herein in its entirety.

BACKGROUND OF THE INVENTION

The present invention relates to arteriovenous grafts and methods for implanting the same. It relates in various embodiments to an arteriovenous graft that has a stepped down venous end, an arteriovenous graft having a cuff for attachment to a target vein and methods relating thereto that include inserting the venous end of a graft into the target vein for positioning downstream of the venotomy site.

Approximately 40,000 new patients per year begin hemodialysis. This number continues to rise annually at a rate of about 10 percent. It has been reported that creation and maintenance of hemodialysis access accounted for approximately $800 million in physician and hospital expenditures in 1998. The term "access" identifies a location within a patient's circulatory system that is specifically configured to act as a site for supplying blood to a dialysis machine and for receiving blood returning from a dialysis machine. Preferred modes of access, if the patient's condition allows, are grafts or fistulas, each of which is a subcutaneous device in fluid communication with the patient's circulatory system into which needles can be repeatedly inserted for transferring blood to and from a dialysis machine during dialysis treatments.

The most common cause of a hospital admission for dialysis patients is an access-related problem, and the cost and frustration of access failure is expected to continue to rise until a solution to the current access problem is identified and instituted. Even in view of this great need, no major advances in hemodialysis access have occurred in the last 30 years. Hakim and Himmelfarb, in their article entitled "Hemodialysis Access Failure: A Call to Action," concluded by saying, "as far as [hemodialysis] access, we can no longer continue doing the same thing (very little indeed), the same way..., and expect that the lives of our [end stage renal disease] patients will be better or that the cost of access care will diminish." Hakim R, Himmelfarb J. *Hemodialysis Access Failure: A Call to Action*, Kidney International Vol 54, (1998), pp. 1029–1040. If the patency rate of an access could be doubled, hundreds of millions of dollars would be saved annually and could be in turn directed toward transplant programs or a cure for renal disease. In addition, dialysis patients, particularly patients suffering from end stage renal disease ("ESRD"), would then be able to enjoy more productive, healthy and happy lives.

A primary arteriovenous fistula (AVF) is the preferred and most cost-effective long-term access for hemodialysis patients. An AVF is an artificial direct connection between an artery and a vein. High blood flow through this connection causes the vein to become much larger and develop a thicker wall, more like an artery. The AVF thus provides a high blood-flow site for accessing the circulatory system for performing hemodialysis. For each dialysis, two large-bore needles (normally 14–16 gauge) are inserted through the dialysis patient's skin and into the AVF, one on the "arterial" end and the other on the "venous" end. When the tips of the needles are properly resting inside the access, a column of blood enters the end of tubing attached to each needle. Prior to beginning a dialysis treatment, a cap is removed from each tubing, thereby allowing blood to fill the tubing, and then a syringe of saline is injected through each tubing and needle. The two needles are then connected with rubber tubing to the inflow (arterial) and outflow (venous) lines of the dialysis machine, and dialysis is started.

Unfortunately, even with careful physical examination and/or the use of doppler ultrasound or venography to identify suitable veins, it has been reported that approximately 40–50% of patients do not have the vascular anatomy sufficient to create a primary AVF. In addition, many dialysis veterans, for whom the use of an AVF has previously failed, can no longer be considered candidates for a primary fistula.

The next option for long-term access is the placement of an arteriovenous graft ("AVG"). An AVG is a length of plastic tube, usually made of porous polytetrafluoroethylene ("PTFE"), which is surgically placed under the skin, fluidly connecting an artery and a vein. Once a graft is placed, a dialysis machine can be fluidly connected to the patient's circulatory system by inserting needles into the graft and connecting the needles to the dialysis machine with tubing as described generally above in connection with an AVF. The phrase "long-term access," however, is a misnomer when discussing an AVG, because reported patency rates are very low, with one-year patency rates of only 40% frequently reported. Even with graft surveillance and aggressive prophylactic measures to prevent thrombosis, primary and secondary patency rates remain low; and the additional costs incurred are also thought to be unreasonably high.

Although many factors have a role in the limited durability of PTFE grafts, enemy number one is the progressive development of neointimal hyperplasia (NIH) with venous anastomotic narrowing and subsequent graft thrombosis. Thrombosed grafts can be declotted surgically or percutaneously, or elaborate atherectomy devices, angioplasties, or stenting procedures can be utilized; but still, the NIH will predictably recur. A revision of the graft with a more proximal anastomosis can also be completed but this too has been found to be very susceptible to failure. There is a great need to improve the patency rates of AVGs to decrease cost and improve patient quality of life.

Neointimal hyperplasia is thought to occur because of many factors, including, for example, injury to endothelium with release of growth factors, turbulent flow at the anastomotic site, vibratory forces on the anastomosis, shear forces, uremia, and other hypothetical etiologies. A multitude of studies show the persistent and consistent development of NIH at the venous anastomotic site.

Physicians have used stepped and tapered grafts, which typically have a gradually increasing diameter along a portion of the graft or along the entire length of the graft from the arterial end to the venous end, and which terminate at the venous end with an opening at a point having the greatest diameter of the graft. An example of a tapered graft having a continuously increasing diameter is set forth in FIG. 1, wherein the diameter of the lumen at venous end 1 is larger than the diameter at the arterial end 2.

A general belief that has become widespread among medical practitioners is that the development of NIH could be prevented or delayed by increasing the size of the venous anastomosis. In an attempt to improve AVG durability, "hooded grafts" with a large venous anastomosis have been utilized. A representative example of a prior art hooded graft (Venaflo, Impra Company) is set forth in FIG. 2, wherein the venous end 3 has a "hood" configuration. However, no significant improvement has been reported resulting from the use of such a hooded graft. Indeed, the Venaflo graft has been found in some cases to occlude sooner than a standard stepped graft. Furthermore, attempts to salvage the graft by surgical or nonsurgical thrombectomy have been found to be more difficult to accomplish and have been found to result in comparatively shorter secondary patency rates.

In view of the above, there is a great need for alternative modes of treatment and care of hemodialysis patients. In particular, a great need exists for new hemodialysis access grafts and methods for surgically placing the same. These needs are addressed by the present invention.

SUMMARY OF THE INVENTION

The present invention addresses problems associated with hemodialysis access grafts known in the prior art by providing novel grafts and methods for surgically placing the same. The embodiments of the invention exhibit a variety of excellent features.

One form of the present invention is a unique arteriovenous graft having a stepped down venous end. The venous end can include a section of generally constant diameter that is adjacent a stepped section of increasing diameter, which is in turn adjacent a section of a larger generally constant diameter. Alternatively, the stepped section can begin at the venous end and have an increasing diameter to an adjacent section of larger diameter. The stepped section can vary in length and slope, and can provide a generally linear increase in diameter or a nonlinear increase. Another form of the invention is an arteriovenous graft that also has a stepped down arterial end.

Another form is a unique arteriovenous graft having a cuff positioned a preselected distance from the venous end for attachment to the wall of a target vein. The cuff defines a groove for receiving a purse-string suture in the vein wall. The cuff can be a single unit affixed to the exterior surface of the graft or can include a plurality of units. In one embodiment, the cuff comprises two rings about the circumference of the graft at a preselected position that are spaced from one another to provide a groove therebetween for receiving the suture and vein wall.

Another form of the invention includes a method for implanting an arteriovenous graft that includes making an incision (venotomy) in the wall of a target vein, inserting the venous end of an inventive graft into the vein such that the venous end is positioned downstream of the venotomy site, and securing the graft to the vein wall. In an embodiment in which a cuffed graft is used, the securing includes making a purse-string suture that engages the groove of the cuff.

It is one object of the invention to provide novel arteriovenous grafts and methods for implanting the same that provide an alternative to the unsatisfactory grafts and methods of the prior art.

Further forms, embodiments, objects, advantages, benefits, aspects and features of the present invention will be apparent from the drawings and detailed description herein.

BRIEF DESCRIPTION OF THE FIGURES

Although the characteristic features of this invention will be particularly pointed out in the claims, the invention itself, and the manner in which it may be made and used, may be better understood by referring to the following descriptions taken in connection with the accompanying figures forming a part hereof.

DESCRIPTION OF PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alternations and further modifications in the invention, and such further applications of the principles of the invention as described herein being contemplated as would normally occur to one skilled in the art to which the invention pertains.

The present invention provides in one aspect an arteriovenous vascular graft prosthesis (hereinafter "graft") comprising a generally tubular conduit defining a lumen for passage of blood and having a tapered or stepped-down venous end. The venous end is configured for insertion inside a target vein at the venotomy site to direct blood flow away from the venotomy site and to provide for a more laminar flow of blood from the graft into the vein to thereby decrease turbulent flow at the anastomotic site.

Figure 1:
FIG. 1 depicts a prior art standard tapered graft.
Figure 2:
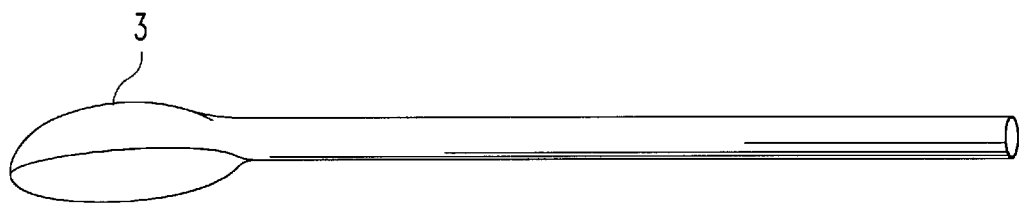
FIG. 2 depicts a prior art hooded graft.
Figure 3:
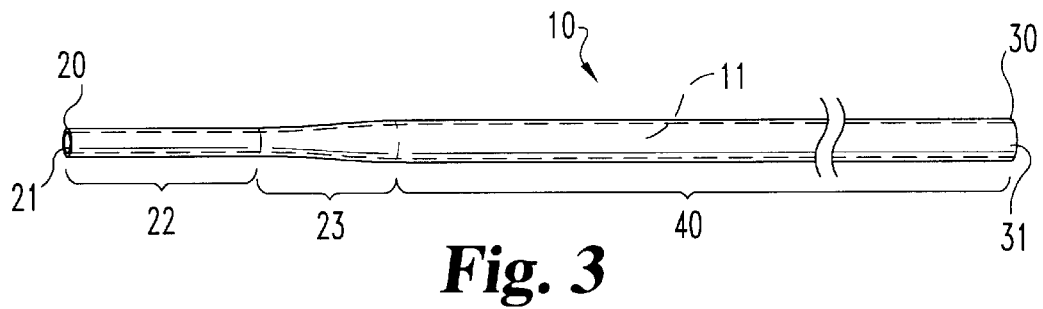
FIG. 3 is a side view of an embodiment of an arteriovenous graft in accordance with the invention.

Referring to FIG. 3, which illustrates one embodiment of the invention, graft 10 has a first end 20 adapted for attachment to a vein (referred to herein as the "venous end") and a second end 30 adapted for attachment to an artery (referred to herein as the "arterial end"). Graft 10 is preferably made of a material having a generally uniform thickness, and graft 10 therefore defines a lumen 11 having generally the same shape as the external surface of the graft.

In graft 10, venous end 20 defines orifice 21 and arterial end 30 defines orifice 31. Orifice 21 and the portion of the graft lumen defined by section 22 of graft 10 have a generally constant diameter that is less than the diameter of orifice 31 and the portion of the graft lumen defined by section 40 of graft 10. The portion of the graft lumen 11 defined by section 23, also referred to herein as a "stepped" section or a "taper" section, has a generally gradually increasing diameter, also described herein as a generally continuous taper, from a longitudinal point adjacent section 22 to a longitudinal point adjacent section 40.

In one embodiment, the portion of graft lumen 11 defined by section 40 has a diameter at least about 20% greater than that defined by section 22. In another embodiment, the portion of graft lumen 11 defined by section 40 has a diameter at least about 30% greater than that defined by section 22. In another embodiment, the portion of graft lumen 11 defined by section 40 has a diameter at least about 40% greater than that defined by section 22. In another embodiment, the portion of graft lumen II defined by section 40 has a diameter at least about 50% greater than that defined by section 22.

In one embodiment, the portion of lumen 11 defined by section 22 has an inner diameter of no greater than about 6 millimeters. In another embodiment, the portion of lumen 11 defined by section 22 has an inner diameter of no greater than about 5 millimeters. In another embodiment, the portion of lumen 11 defined by section 22 has an inner diameter of from about 3.5 to about 4.5 millimeters and the portion of lumen 11 defined by section 40 has an inner diameter of from about 5.5 to about 7.0 millimeters.

In one embodiment, section 23 extends for a relatively short length of graft 10, such as, for example, less than about 2 centimeters. In such an embodiment, section 23 is preferably positioned from about 1 to about 10 centimeters from venous end 20. In another embodiment, section 23 is positioned from about 1 to about 8 centimeters from venous end 20, and in yet another embodiment, section 23 is positioned from about 1 to about 6 centimeters from venous end 20.

In another embodiment, section 23 extends along a greater length of the graft, such as, for example, greater than about 2 centimeters, thereby providing a more gradual taper. In one embodiment, section 23 extends along a length of the graft of from about 1 to about 10 centimeters.

Figure 4:
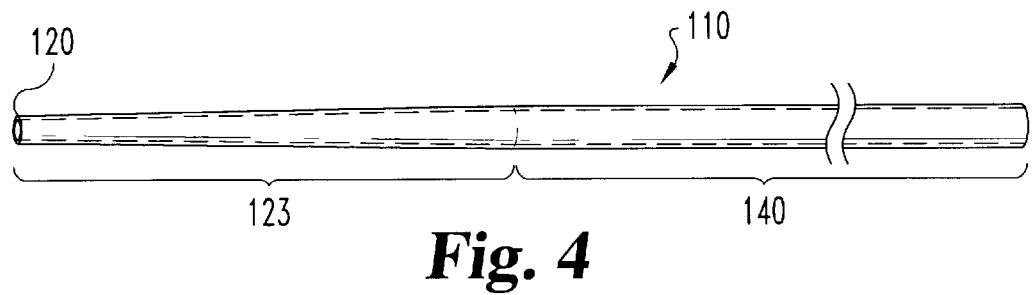
FIG. 4 is a side view of another embodiment of an arteriovenous graft in accordance with the invention.

In another embodiment, depicted in FIG. 4, graft 110 does not include a section corresponding to section 22 in FIG. 3, and stepped section 123 generally continuously tapers from venous end 120 to section 140 of greater diameter. In one embodiment, section 123 extends along the longitudinal axis of graft 110 to a longitudinal point at least about 4 centimeters from venous end 120. In another embodiment, section 123 extends along the longitudinal axis of graft 110 to a longitudinal point from about 4 centimeters to about 15 centimeters from venous end 120. In another embodiment, section 123 extends along the longitudinal axis of graft 110 to a longitudinal point from about 4 centimeters to about 10 centimeters from venous end 120.

Figure 5:
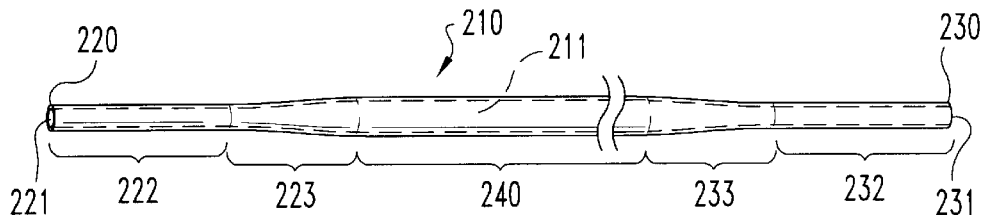
FIG. 5 is a side view of another embodiment of an arteriovenous graft in accordance with the invention.

Referring now to FIG. 5, in another embodiment of the invention, in addition to having a stepped-down venous end, graft 210 also has a stepped-down arterial end. Graft 210 has a first end 220 adapted for attachment to a vein and a second end 230 adapted for attachment to an artery. In graft 210, venous end 220 defines orifice 221 and arterial end 230 defines orifice 231. Orifice 221 and the portion of the graft lumen defined by section 222 of graft 210 have a generally constant diameter that is less than the diameter of the portion of the graft lumen defined by section 240 of graft 210. In addition, orifice 231 and the portion of the graft lumen defined by section 232 of graft 210 have a generally constant diameter that is less than the diameter of the portion of the graft lumen defined by section 240 of graft 210. The portion of the graft lumen 211 defined by section 223, also referred to herein as a "stepped" section or a "taper" section, has a generally gradually increasing diameter from the longitudinal point adjacent section 222 to the longitudinal point adjacent section 240, also described herein as a generally continuous taper. Similarly, the portion of the graft lumen 211 defined by section 233, also referred to herein as a "stepped" section or a "taper" section, has a generally evenly increasing diameter from the longitudinal point adjacent section 232 to the longitudinal point adjacent section 240.

In one embodiment, the portion of graft lumen 211 defined by section 240 has a diameter at least about 20% greater than that defined by section 222 or section 232. In another embodiment, the portion of graft lumen 211 defined by section 240 has a diameter at least about 30% greater than that defined by section 222 or section 232. In another embodiment, the portion of graft lumen 211 defined by section 240 has a diameter at least about 40% greater than that defined by section 222 or section 232. In another embodiment, the portion of graft lumen 211 defined by section 240 has a diameter at least about 50% greater than that defined by section 222 or section 232. In another embodiment, the portion of graft lumen 211 defined by section 240 has a length that is at least about 50% of the length of the graft. In another embodiment, the portion of graft lumen 211 defined by section 240 has a length that is at least about 60% of the length of the graft. In another embodiment, the portion of graft lumen 211 defined by section 240 has a length that is at least about 70% of the length of the graft. In another embodiment, the portion of graft lumen 211 defined by section 240 has a length that is at least about 80% of the length of the graft.

In one embodiment, the portion of lumen 211 defined by section 222 has an inner diameter of no greater than about 6 millimeters. In another embodiment, the portion of lumen 211 defined by section 222 has an inner diameter of no greater than about 5 millimeters. In another embodiment, the portion of lumen 211 defined by section 232 has an inner diameter of no greater than about 6 millimeters. In another embodiment, the portion of lumen 211 defined by section 232 has an inner diameter of no greater than about 5 millimeters. In another embodiment, the portions of lumen 211 defined by section 222 and section 232 each have an inner diameter of from about 3.5 to about 4.5 millimeters and the portion of lumen 211 defined by section 240 has an inner diameter of from about 5.5 to about 7.5 millimeters. In another embodiment, the portions of lumen 211 defined by section 222 and section 232 each have an inner diameter of from about 3.5 to about 4.5 millimeters and the portion of lumen 211 defined by section 240 has an inner diameter of from about 5.5 to about 6.5 millimeters. In another embodiment, the portions of lumen 211 defined by section 222 and section 232 each have an inner diameter of about 4 millimeters and the portion of lumen 211 defined by section 240 has an inner diameter of about 6 millimeters.

Sections 223 and 233 can extend for a relatively short length of graft 210, such as, for example, less than about 2 centimeters each. In such an embodiment, section 223 is preferably positioned from about 1 to about 10 centimeters from venous end 220 and section 233 is preferably positioned from about 1 to about 10 centimeters from arterial end 230. In another embodiment, section 223 is positioned from about 1 to about 8 centimeters from venous end 220, and section 233 is positioned from about 1 to about 8 centimeters from arterial end 230. In yet another embodiment, section 223 is positioned from about 1 to about 6 centimeters from venous end 220 and section 233 is positioned from about 1 to about 6 centimeters from arterial end 230.

Alternatively, sections 223 and 233 can each extend along a greater length of the graft, such as, for example, greater than about 2 centimeters, thereby providing a more gradual taper. In one embodiment, sections 223 and 233 each extend along a length of the graft of from about 2 to about 10 centimeters.

Figure 6:
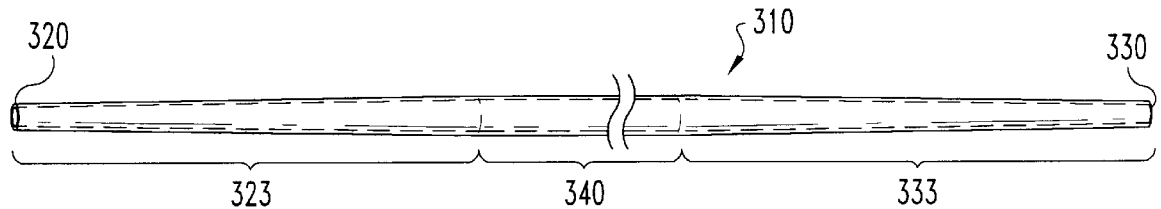
FIG. 6 is a side view of another embodiment of an arteriovenous graft in accordance with the invention.

In another embodiment, depicted in FIG. 6, graft 310 does not include sections corresponding to sections 222 and 232 in FIG. 5. Rather, stepped section 323 generally continuously tapers from venous end 320 to section 340 of greater diameter and stepped section 333 generally continuously tapers from arterial end 330 to section 340 of greater diameter. Sections 323 and 333 each preferably extend along the longitudinal axis of graft 310 to a longitudinal point at least about 4 centimeters from respective ends 320 and 330. In one embodiment, sections 323 and 333 each extend along the longitudinal axis of graft 310 to a longitudinal point from about 4 centimeters to about 15 centimeters from respective ends 320 and 330. In another embodiment, sections 323 and 333 each extend along the longitudinal axis of graft 310 to a longitudinal point from about 4 centimeters to about 10 centimeters from respective ends 320 and 330.

Grafts described herein are preferably made from polytetrafluoroethylene ("PTFE"); however, it is not intended that the invention be limited by the material from which the graft is made. It is contemplated that the graft can advantageously be made from a wide variety of biocompatible materials, now known or later developed, having acceptable physical characteristics of flexibility and the like.

Figure 7:
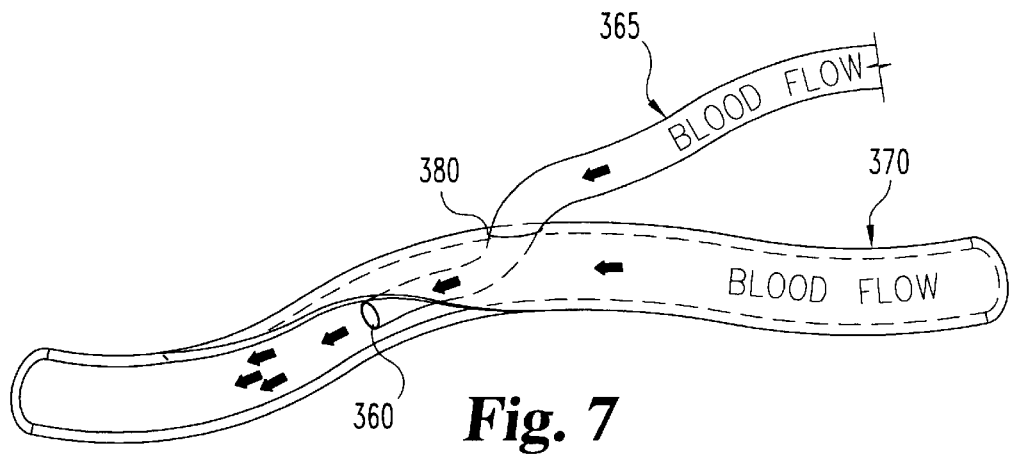
FIG. 7 is a partial cutaway side view of an inventive graft after implantation of the graft.

Also provided by the present invention are methods for surgically implanting inventive grafts. To place a graft in accordance with the invention, an incision is made in a target vein, the venous end of the graft is introduced into the interior of the vein and placed a predetermined distance downstream from the venotomy, and the graft is sealingly secured to the vein wall. A representative configuration of the graft in relation to the target vein after placement is depicted in FIG. 7, in which the venous end 360 of graft 365 is positioned within the target vein 370 at a location downstream from the venotomy site 380 relative to the natural flow of blood in the vein 370.

In one embodiment, a venous anastomosis is achieved by (1) making an incision in the wall of a preselected target vein; (2) inserting the venous end of an inventive graft through the incision into the vein such that the first end passes to a point downstream of the incision; (3) securing the graft to the vein; and (4) anastomosing the arterial end to a preselected target artery. In one embodiment, the graft can be advantageously secured to the vein using a purse-string suture. In one manner of practicing the invention, the purse-string suture can be inserted in a wall of the target vein prior to making the incision. In another embodiment, the inserting includes inserting the venous end of an inventive graft through the incision into the vein such that the venous end passes to a point at least about 1 centimeter downstream of the incision. In another embodiment, the inserting includes inserting the venous end of an inventive graft through the incision into the vein such that the venous end passes to a point from about 1 to about 4 centimeters downstream of the incision. In another embodiment, the inserting includes inserting the venous end of an inventive graft through the incision into the vein such that the venous end passes to a point from about 1 to about 3 centimeters downstream of the incision. Inserting the venous end of the graft into the vein directs blood flow away from the venotomy site and therefore decreases the violent flow of blood at the anastomotic site.

One advantage of the invention is that the venous end of an inventive graft can be placed in veins having a wide variety of sizes, including veins that were previously thought to be unavailable due to size limitations. In one manner of practicing the invention, the vein selected for anastomosis has a diameter of no greater than about 1.5 centimeters. In another embodiment, the selected vein has a diameter of from about 0.4 centimeters to about 1.5 centimeters. In another embodiment, the selected vein has a diameter of no greater than about 1.4 centimeters. In another embodiment, the selected vein has a diameter of no greater than about 1.3 centimeters. In another embodiment, the selected vein has a diameter of no greater than about 2 centimeters. It is also contemplated that the invention can be used for placement of an inventive graft in a large vein, such as a vein in a patient's leg. As such, in another embodiment, the selected vein has a diameter of up to about 3 centimeters.

In another aspect, the invention provides a graft that includes a cuff positioned a desired distance from the venous end of the graft and adapted to receive a purse-string suture at the venotomy site during the surgical placement of the graft, thereby isolating injured endothelium at the site of the venotomy from the intravascular portion of the anastomosis. In this regard, in one aspect of the invention, a graft is provided that includes a cuff affixed to the outer surface of the graft, the cuff defining a groove configured to receive a purse-string suture for a venous anastomosis. It is to be understood that the present invention contemplates the use of such cuffs in connection with novel grafts described herein having a tapered or stepped down venous end as well as standard grafts, i.e., grafts that are not tapered at the venous end, and other grafts.

Figure 9:
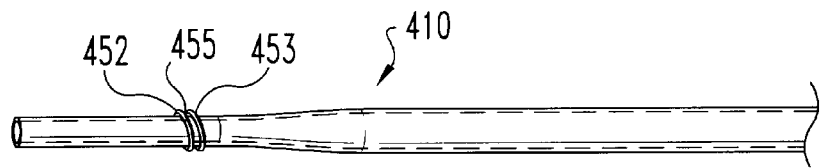
FIG. 9 is a side view of another embodiment of an arteriovenous graft in accordance with the invention.
Figure 10:
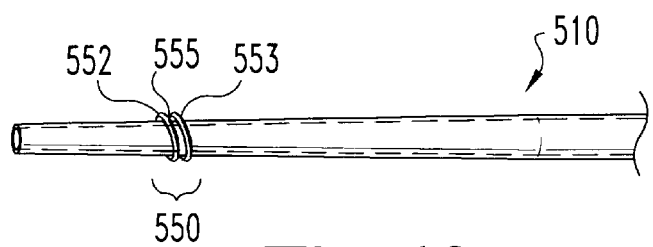
FIG. 10 is a side view of another embodiment of an arteriovenous graft in accordance with the invention.

In one embodiment, the cuff is configured such that the groove lies on a plane that is generally perpendicular to a longitudinal axis of the graft. It is readily understood that with this arrangement, when the graft is sutured to a vein wall, the graft will pass through the vein wall generally at a 90 degree angle to the vein. In another embodiment, the cuff is configured such that the groove lies on a plane that is at an angle to a longitudinal axis of the graft, as shown in FIGS. 9 and 10. In one preferred embodiment, the groove lies on a plane that is at an angle of about 45 degrees to the longitudinal axis of the graft; however, the invention contemplates a wide variety of angles.

Figure 8:
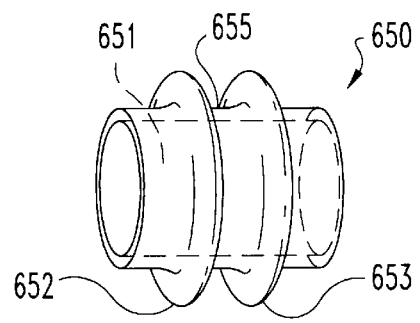
FIG. 8 is a side view of an embodiment of a cuff in accordance with the invention.

In one embodiment, the cuff includes a single structure defining a groove. For example, FIG. 8 depicts a cuff 650 configured for attachment to the external surface of a graft. Cuff 650 defines a lumen 651 that is sized to engage the external surface of a graft at a desired location. Cuff 650 also includes a first ridge 652 and a second ridge 653 extending around the circumference of cuff 650 and forming a groove 655 therebetween. Cuff 650 can be attached to a graft using a biocompatible adhesive or can be integrally formed to a graft.

In another embodiment, the cuff can include two ring structures about the circumference of a graft and defining a groove therebetween. Referring now to FIGS. 9 and 10, grafts 410, 510 include cuffs 450, 550 affixed or integrally molded to the outer surface of grafts 410, 510, respectively. Cuffs 450, 550 each include two ring structures 452, 453, 552, 553 and each define a groove, 455, 555 configured to receive a purse-string suture for a venous anastomosis.

In one embodiment, the groove is positioned at least about 1 centimeter from the venous end. In another embodiment, the groove is positioned from about 1 centimeter to about 5 centimeters from the venous end. In another embodiment, the groove is positioned from about 1 to about 3 centimeters from the venous end. It is readily understood that the distance from the venous end affects the length of the graft that resides inside the target vein after completion of a graft implantation procedure. In one embodiment, for example, a cuff is positioned such that the groove defined by the cuff is positioned from about 1 to about 3 centimeters from the venous end of the graft. In another embodiment, a cuff is positioned such that the groove defined by the cuff is positioned from about 1.5 to about 2.5 centimeters from the venous end of the graft. In another embodiment, wherein the cuff includes two ring structures as shown in FIGS. 9 and 10, one ring is positioned about 1.75 centimeters from the venous end of the graft and another ring is positioned about 2.25 centimeters from the venous end, defining the grove therebetween.

Figure 11:
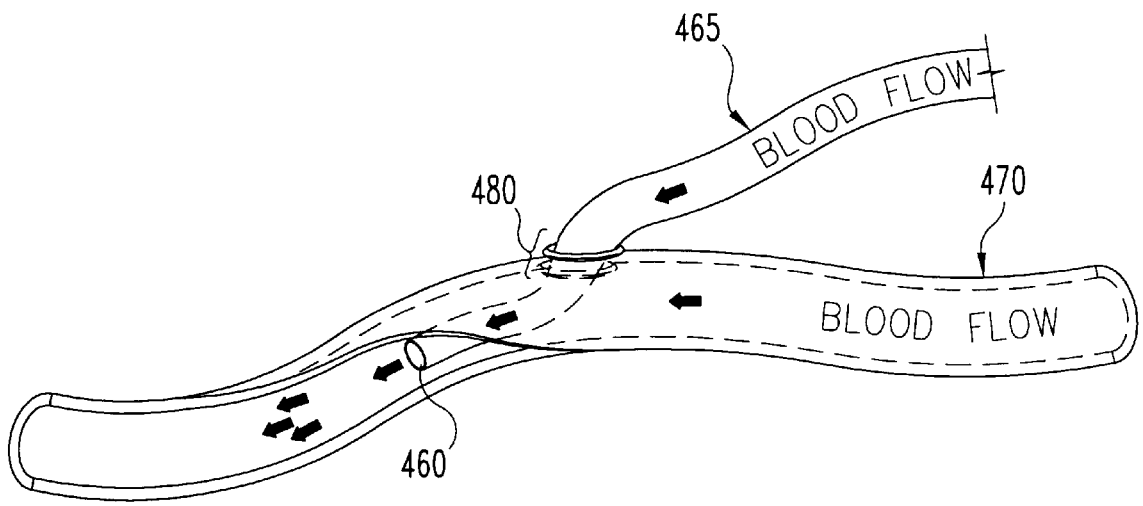
FIG. 11 is a partial cutaway side view of an inventive graft after implantation of the graft.

Also provided by the present invention are methods for implanting inventive grafts having cuffs as described herein. To place a graft having a cuff in accordance with the invention, an incision is made in a target vein, the venous end of the graft is introduced into the interior of the vein such that the cuff is positioned whereby the groove is positioned to receive the vein wall at the venotomy site, and the vein wall is secured to the graft. A representative configuration of a cuffed graft in relation to the target vein after placement is depicted in FIG. 11, in which the venous end 460 of graft 465 is positioned within the target vein 470 at a location downstream from the venotomy site relative to the natural flow of blood in the vein 470. The cuff 480 is positioned so that the groove defined thereby receives the wall of vein 470 at the venotomy site.

In one embodiment, a venous anastomosis is achieved by (1) making an incision in the wall of a preselected target vein; (2) inserting the venous end of a cuffed graft through the incision into the vein such that the groove is positioned to receive the vein wall and a suture; (3) securing the vein wall to the cuff; and (4) anastomosing the second end to a preselected target artery. In one embodiment, the venous end of the graft can be advantageously secured to the vein using a purse-string suture. In one manner of practicing the invention, the purse-string suture can be inserted in a wall of the target vein prior to making the incision and the securing includes securing the vein wall to the cuff using the purse-string suture. In addition to directing the blood flow away from the venotomy, reducing the forces of the graft on the anastomotic site, and making the blood flow more laminar, use of the present invention also significantly reduces the amount of injury to the vein endothelium produced by the venotomy and suturing. Furthermore, constructing a venous anastomosis using a cuff and purse-string suture in accordance with the invention allows isolation of the venotomy itself (i.e., the cut edges of the vein wall) from the interior of the vein. Thus, blood in the graft and vein does not come into contact with the venotomy site.

It is to be understood that the present invention also contemplates the use of cuffs in connection with standard grafts, i.e., grafts that are not tapered at the venous end. In addition, although embodiments including cuffs are described and shown herein, it is not intended that the invention be limited to grafts having cuffs, and the present invention in certain aspects as described above, provides configurations that do not include cuffs. Where a cuff is absent, the graft can be anastomosed to the vein using other techniques known in the art, and the graft optionally can include alternative structures for attachment to the vein as are known in the art.

Thus, in one embodiment of the invention, a graft includes (1) a first end adapted for placement in a vein and defining a first orifice having a first diameter; (2) a second end adapted for attachment to an artery; (3) a first tubular section between the first and second ends, the first tubular section defining a portion of the lumen having a second, generally constant diameter greater than the first diameter; and (4) a first taper section between the first end and the first tubular section, and having a generally gradually increasing diameter along the first taper section. In another embodiment, a graft includes a second tubular section between the first end and the first taper section, the second tubular section defining a portion of the lumen having a generally constant diameter corresponding to the first diameter.

In a further embodiment, the arterial end of a graft defines a second orifice having a third diameter less than the second diameter and the graft includes a second taper section between the first tubular section and the second end, the second taper section having a generally evenly decreasing diameter. In still a further embodiment, a graft includes a third tubular section between the arterial end and the second taper section, wherein the third tubular section defines a portion of the lumen having a generally constant diameter corresponding to the third diameter.

In another embodiment, a cuff is affixed to the outer surface of the graft at least about 1 centimeter from the first end, the cuff defining a groove configured to receive a purse-string suture for a venous anastomosis. In yet a further embodiment, the groove lies generally on a plane that is at an angle of about 45 degrees to a longitudinal axis of the graft. The cuff in one embodiment includes a tubular member defining a lumen sized to engage an external surface of the graft; and first and second ridges extending around the member and defining the groove therebetween. In another embodiment, the cuff includes a first ring member affixed to the graft; and a second ring member affixed to the graft; wherein the first and second ring members define the groove therebetween.

Another form of the invention is a method, including (1) making an incision in the wall of a preselected target vein; (2) providing an inventive arteriovenous graft; (3) inserting the first end (venous end) of the graft through the incision into the vein such that the first end passes to a point downstream of the incision; (4) securing the graft to the vein wall; and (5) anastomosing the arterial end of the graft to a preselected target artery.

In another form of the invention, the graft is secured to the vein using a purse-string suture. In another form of the invention, the purse-string suture is inserted in a wall of the target vein prior to making the incision. In yet another form of the invention, the inserting includes inserting the first end through the incision into the vein such that the first end passes to a point at least about 1 centimeter downstream of the incision. In another embodiment of the invention, the graft includes a cuff affixed to the outer surface of the graft at least about 1 centimeter from the first end, the cuff defining a groove configured to receive a purse-string suture for a venous anastomosis. In this embodiment, the inserting includes inserting the first end of the graft through the incision into the vein such that the groove is positioned to receive the vein wall and the securing includes securing the vein wall to the cuff. In still another manner of practicing the invention, a purse-string suture is inserted in a wall of the target vein prior to making the incision and the securing includes drawing the purse-string suture into the groove.

As noted above, one advantage of the invention is that use of a graft having a tapered or stepped down venous end enables a reduction in the size of the venotomy, which is expected to decrease the amount of endothelial injury and dampen the cascade leading to NIH. Furthermore, in embodiments including a cuff on the graft, a purse-string suture anastomosis can exclude the injured endothelium from the intravascular portion of the anastomosis. The cuff can also prevent slipping or dislodgment of the pursestring anastomosis which could result in obvious disastrous results.

Decreasing the diameter of the graft at the exit also serves to dampen turbulent flow and make flow more laminar.

Though it is apparent that a tapering of the venous end will have an effect upon blood flow rates and pressures within an inventive graft, it is believed that inventive grafts will exhibit excellent long-term flow characteristics while also exhibiting other advantages apparent from the present description. Indeed, researchers conducting graft surveillance studies have reported that a large percentage of functioning AVGs have anastomotic or other stenoses greater than 50% of the original diameter. Other researchers have stated that the "critical stenosis for thrombosis is about a 70% decrease in diameter." Hakim and Himmelfarb (1998). In an inventive graft having a 4 millimeter venous end that is stepped down from a 6 millimeter section, the diameter indeed decreases at the venous end, but only by 33%. In addition, in embodiments that are tapered at each end (i.e., at the venous end and the arterial end), it is believed that volumetric flow rate through the graft will not be significantly altered by having a stepped down venous end.

It is expected that resistance to flow resulting from having a tapered venous end will result in a decreased rate of flow within the portion of the graft having a larger diameter. It has been reported that a flow greater than 800 ml per min is critical to prevent thrombosis. Hakim and Himmelfarb (1998). It is believed, for reasons stated above, that an inventive graft would remain patent for an acceptable period of time with an adequate blood pressure and arterial inflow. Although there is some possibility that thrombosis in the larger diameter portion of an inventive graft resulting from a reduced rate of flow may be a concern in the use of inventive grafts, it is expected that an increased tendency toward thrombosis, if present, can be addressed by using anticoagulants and/or antiplatelet drugs.

In addition, Lumsden commented that the length of a segment having a 4 millimeter diameter on a stepped graft at the arterial anastomosis might adversely affect patency if greater than 2 centimeters. The difference, if statistically significant, was not outlined; but this would be consistent with Poiseuille's Law and with Hakim and Himmelfarb's findings regarding flow rate. In applying the Hagan-Poiseuille Law:

$$Q = \frac{\pi R^4 \Delta P}{8 \eta L}$$

when other variables remain unchanged, as the radius (R) of a tube decreases, the volume flow rate (Q) decreases, and not linearly. As the length (L) (of the narrowed area) increases, the flow rate (Q) also decreases. Lumsden's findings would be expected to apply similarly to the venous end. Therefore, one preferred embodiment of the invention includes a stepped-down venous end portion having dimensions (i.e., radius and length of stepped-down portion) that do not significantly increase the risk of thrombosis of the graft. In one preferred embodiment, the stepped-down venous end portion has a length of no greater than about 3 centimeters. In another embodiment, the stepped-down venous end portion has a length of no greater than about 2 centimeters. In another embodiment, the stepped-down venous end portion has a length of no greater than about 1 centimeter;

As mentioned above, a widespread belief and a current trend is to implant a graft having a relatively large venous anastomosis. The belief and trend is thought to result from the notion that venous end graft occlusion would be delayed in a graft having a large venous anastomosis because a greater degree of stenosis would be required to narrow the venous anastomosis beyond the critical size necessary for patency. A person of ordinary skill in the art would find no motivation in the prior art to use an AVG having a smaller venous end and, indeed, a person of ordinary skill in the art would conclude that a smaller anastomosis would lead to an accelerated point of critical stenosis and occlusion. It is believed that a smaller anastomosis in the classical manner (end to side) would result in the development of NIH and a more abrupt "critical stenosis" with thrombosis; however, the present invention provides unique devices and methods that enable the placement of an AVG having a stepped down or tapered venous end.

All references, including publications, patents, and patent applications, cited or listed in this specification are herein incorporated by reference as if each individual reference were specifically and individually indicated to be incorporated by reference and set forth in its entirety herein. Further, any theory, proposed mechanism of operation, or finding stated herein is meant to further enhance understanding of the present invention, and is not intended to in any way limit the present invention to such theory, proposed mechanism of operation, or finding. While the invention has been illustrated and described in detail in the drawings and foregoing description, the same is to be considered as illustrative and not restrictive in character, it being understood that only the preferred embodiments have been shown and described and that all changes, equivalents, and modifications that come within the spirit of the invention defined by following claims are desired to be protected.

What is claimed is:

1. An arteriovenous graft defining a lumen for passage of blood, comprising:
   a first end defining a first orifice having a first diameter, the first end adapted for placement into a vein with the first orifice positioned at a location spaced downstream from an entry location of the first end into the vein for passage of blood from the lumen into the bloodstream, wherein the first end is adapted to position the first orifice a distance of one to three centimeters from the entry location;
   a second end adapted for attachment to an artery;
   a first tubular section between the first and second ends, the first tubular section defining a portion of the lumen having a second, generally constant diameter greater than the first diameter; and
   a first taper section between said first end and said first tubular section, and having a generally gradually increasing diameter along the first taper section.

2. The graft in accordance with claim 1, wherein the second diameter is at least about 20% greater than the first diameter.

3. The graft in accordance with claim 1, wherein the second diameter is at least about 30% greater than the first diameter.

4. The graft in accordance with claim 1, wherein the first diameter is no greater than about 6 millimeters.

5. The graft in accordance with claim 1, wherein the first diameter is no greater than about 5 millimeters.

6. The graft in accordance with claim 1, wherein the first diameter is from about 3.5 to about 4.5 millimeters and wherein the second diameter is from about 5.5 to about 7.0 millimeters.

7. The graft in accordance with claim 1, further comprising a second tubular section between said first end and said first taper section, said second tubular section defining a portion of the lumen having a generally constant diameter corresponding to the first diameter.

8. The graft in accordance with claim 7, wherein said second tubular section includes a longitudinal length of from about one 1 to 3 centimeters from said first end to said first taper section.

9. The graft in accordance with claim 7, wherein the longitudinal length of the first taper section is: less than about 2 centimeters.

10. The graft in accordance with claim 7, wherein the first taper section is positioned from about 1 to about 10 centimeters from said venous end.

11. The graft in accordance with claim 1, wherein the longitudinal length of the first taper section is from about 2 to about 10 centimeters.

12. The graft in accordance with claim 1, wherein the first taper section extends from said venous end to a longitudinal point at least about 4 centimeters from said venous end.

13. The graft in accordance with claim 1, wherein the first taper section extends from said venous end to a longitudinal point from about 4 to about 15 centimeters from said venous end.

14. The graft in accordance with claim 1, wherein said arterial end defines a second orifice having a third diameter less than the second diameter; and said graft further comprising a second taper section between said first tubular section and said second end, the second taper section having a generally evenly decreasing diameter.

15. The graft in accordance with claim 14, further comprising a third tubular section between said arterial end and said second taper section, wherein said third tubular section defines a portion of the lumen having a generally constant diameter corresponding to the third diameter.

16. The graft in accordance with claim 15, wherein the second diameter is at least about 20% greater than the third diameter.

17. The graft in accordance with claim 15, wherein the third diameter is no greater than about 6 millimeters.

18. The graft in accordance with claim 15, wherein the first diameter is from about 3.5 to about 4.5 millimeters; wherein the second diameter is from about 5.5 to about 6.5 millimeters; and wherein the third diameter is from about 3.5 to about 4.5 millimeters.

19. The graft in accordance with claim 14, wherein said first tubular section has a length that is at least about 60% of the length of the graft.

20. The graft in accordance with claim 14, wherein said first tubular section has a length that is at least about 70% of the length of the graft.

21. The graft in accordance with claim 14, wherein said first tubular section has a length that is at least about 80% of the length of the graft.

22. The graft in accordance with claim 1, further comprising a cuff affixed to the outer surface of the graft at least about 1 centimeter from said first end, the cuff defining a groove configured to receive a purse-string suture in the vein wall for a venous anastomosis.

23. The graft in accordance with claim 22, wherein the groove lies generally on a plane that is at an angle of about 45 degrees to a longitudinal axis of the graft.

24. The graft in accordance with claim 22, wherein said cuff is positioned from about 1 to about 10 centimeters from said first end.

25. The graft in accordance with claim 22, wherein said cuff is positioned from about 1 to about 5 centimeters from said first end.

26. The graft in accordance with claim 22, wherein said cuff comprises:
 a tubular member defining a lumen sized to engage an external surface of said graft; and
 first and second ridges extending around said member and defining the groove therebetween.

27. The graft in accordance with claim 22, wherein said cuff comprises:
 a first ring member affixed to said graft; and
 a second ring member affixed to said graft;
 wherein the first and second ring members define the groove therebetween.

28. The graft in accordance with claim 27, wherein the first ring is positioned from about 1.5 to about 2 centimeters from the first end and wherein the second ring is positioned from about 2 to about 2.5 centimeters from the first end.

29. The graft in accordance with claim 27, wherein the first ring is positioned about 1.75 centimeters from the first end and wherein the second ring is positioned about 2.25 centimeters from the first end.

30. An arteriovenous graft defining a lumen for passage of blood, comprising:
 a first end defining a first orifice having a first diameter, the first end adapted for placement into a vein with the first orifice positioned at a location spaced downstream from an entry location of the first end into the vein for passage of blood from the lumen into the bloodstream, wherein the first end is adapted to position the first orifice a distance of one to three centimeters from the entry location;
 a second end adapted for attachment to an artery; and
 a first tubular section between the first and second ends, the first tubular section defining a portion of the lumen having a second, generally constant diameter greater than the first diameter.

31. The graft in accordance with claim 30, further comprising a first taper section between the first end and the first tubular section, and having a generally gradually increasing diameter along the first taper section.

32. The graft in accordance with claim 31, further comprising a second tubular section between said first end and said first taper section, said second tubular section defining a portion of the lumen having a generally constant diameter corresponding to the first diameter.

33. The graft in accordance with claim 32, wherein said second tubular section includes a longitudinal length from about one to three centimeters from said first end to said first taper section.

34. The graft in accordance with claim 32, wherein said first taper section includes a longitudinal length less than about 2 centimeters.

35. An arteriovenous graft defining a lumen for passage of blood, comprising:
 a first end adapted for placement in a vein through a wall of the vein and defining a first orifice having a first diameter;
 a second end adapted for attachment to an artery;
 a first tubular section between the first and second ends, the first tubular section defining a portion of the lumen having a second, generally constant diameter greater than the first diameter, wherein said second end defines a second orifice having a third diameter less than the second diameter;
 a first taper section between said first end and said first tubular section, and having a generally gradually increasing diameter along the first taper section;
 a second taper section between said first tubular section and said second end, the second taper section having a generally evenly decreasing diameter; and a third tubular section between said arterial end and said second taper section, wherein said third tubular section defines a portion of the lumen having a generally constant diameter corresponding to the third diameter, wherein the first diameter is from about 3.5 to about 4.5 millimeters, the second diameter is from about 5.5 to about 6.5 millimeters, and the third diameter is from about 3.5 to about 4.5 millimeters.

36. An arteriovenous graft defining a lumen for passage of blood, comprising:

a first end adapted for placement in a vein through a wall of the vein and defining a first orifice having a first diameter;

a second end adapted for attachment to an artery;

a first tubular section between the first and second ends, the first tubular section defining a portion of the lumen having a second, generally constant diameter greater than the first diameter, wherein said second end defines a second orifice having a third diameter less than the second diameter;

a first taper section between said first end and said first tubular section, and having a generally gradually increasing diameter along the first taper section;

a second taper section between said first tubular section and said second end, the second taper section having a generally evenly decreasing diameter, wherein said first tubular section has a length that is at least about 60% of the length of the graft.

37. The graft in accordance with claim 36, wherein said first tubular section has a length that is at least about 70% of the length of the graft.

38. The graft in accordance with claim 36, wherein said first tubular section has a length that is at least about 80% of the length of the graft.

39. A method of implantation, comprising:

making an incision in the wall of a preselected target vein;

providing an arteriovenous graft defining a lumen for passage of blood, the graft including:

a first end adapted for placement in a vein through the incision and defining a first orifice having a first diameter;

a second end adapted for attachment to an artery;

a first tubular section between the first and second ends, the first tubular section defining a portion of the lumen having a second, generally constant diameter greater than the first diameter; and a first taper section between said first end and said first tubular section, and having a generally gradually increasing diameter along the first taper section;

inserting the first end through the incision into the vein such that the first end passes to a point downstream of the incision;

securing the graft to the vein wall, wherein the graft is secured to the vein wall using a purse-string suture inserted in a wall of the target vein prior to making the incision; and anastomosing the arterial end of the graft to a preselected target artery.

40. The method in accordance with claim 39, wherein said inserting comprises inserting the first end through the incision into the vein such that the first end passes to a point at least about 1 centimeter downstream of the incision.

41. A method of implantation, comprising:

making an incision in the wall of a preselected target vein;

providing an arteriovenous graft defining a lumen for passage of blood, the graft including:

a first end adapted for placement in a vein through the incision and defining a first orifice having a first diameter;

a second end adapted for attachment to an artery;

a first tubular section between the first and second ends, the first tubular section defining a portion of the lumen having a second, generally constant diameter greater than the first diameter; and a first taper section between said first end and said first tubular section, and having a generally gradually increasing diameter along the first taper section;

inserting the first end through the incision into the vein such that the first end passes to a point downstream of the incision, wherein the first end through the incision into the vein such that the first end passes to a point at least about 1 centimeter downstream of the incision;

securing the graft to the vein wall; and anastomosing the arterial end of the graft to a preselected target artery.

42. The method in accordance with claim 41, wherein the graft is secured to the vein wall using a purse-string suture.

43. The method in accordance with claim 41, wherein the purse-string suture is inserted in a wall of the target vein prior to making the incision.

44. The method in accordance with claim 41, wherein the vein has a diameter of less than about 1.5 centimeters.

45. The method in accordance with claim 41, wherein the vein has a diameter of no greater than about 1.4 centimeters.

46. The method in accordance with claim 41, wherein the vein has a diameter of no greater than about 1.3 centimeters.

47. The method in accordance with claim 41, wherein the vein has a diameter of up to about 3 centimeters.

48. The method in accordance with claim 41, wherein the graft comprises a cuff affixed to the outer surface of the graft at least about 1 centimeter from said first end, the cuff defining a groove configured to receive a purse-string suture for a venous anastomosis;

wherein said inserting comprises inserting the first end of the graft through the incision into the vein such that the groove is positioned to receive the vein wall; and wherein said securing comprises securing the vein wall to the cuff.

49. The method in accordance with claim 48, wherein the vein wall is secured to the cuff using a purse-string suture.

50. The method in accordance with claim 49, wherein the purse-string suture is inserted in a wall of the target vein prior to making the incision and wherein said securing comprises drawing the purse-string suture into the groove.

* * * * *